(12) United States Patent
Maurel (10) Patent No.: US 9,173,838 B2
(45) Date of Patent: *Nov. 3, 2015

(54) REVERSE MICELLE COMPOSITIONS FOR DELIVERY OF METAL CATIONS COMPRISING A DIGLYCERIDE AND A PHYTOSTEROL AND METHOD OF PREPARATION

(75) Inventor: Jean-Claude Maurel, Castries (FR)

(73) Assignee: MEDESIS PHARMA SA, Paris (FR)

( * ) Notice: Subject to any disclaimer, the term of this patent is extended or adjusted under 35 U.S.C. 154(b) by 1997 days.

This patent is subject to a terminal disclaimer.

(21) Appl. No.: 11/718,511

(22) PCT Filed: Nov. 2, 2005

(86) PCT No.: PCT/IB2005/003605
§ 371 (c)(1),
(2), (4) Date: Nov. 24, 2008

(87) PCT Pub. No.: WO2006/048773
PCT Pub. Date: May 11, 2006

(65) Prior Publication Data
US 2009/0087477 A1    Apr. 2, 2009

(30) Foreign Application Priority Data
Nov. 2, 2004 (EP) .................................. 04025987

(51) Int. Cl.
*A61K 31/28* (2006.01)
*A61K 9/107* (2006.01)
*A23L 1/30* (2006.01)

(52) U.S. Cl.
CPC ............. *A61K 9/1075* (2013.01); *A23L 1/3004* (2013.01); *A61K 31/28* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,075,336 | A | * 12/1991 | Czernecki et al. | ............ 514/574 |
| 5,252,333 | A | 10/1993 | Horrobin | |
| 6,129,924 | A | 10/2000 | Maurel et al. | |
| 6,365,176 | B1 | 4/2002 | Bell et al. | |
| 2002/0098275 | A1* | 7/2002 | Bodnar et al. | ................ 426/612 |
| 2002/0120015 | A1* | 8/2002 | Dennis et al. | ............... 514/772.3 |
| 2003/0113366 | A1* | 6/2003 | MacGregor | ................... 424/449 |

FOREIGN PATENT DOCUMENTS

| | | |
|---|---|---|
| EP | 1452175 | 9/2004 |
| FR | 2729957 | 8/1996 |
| WO | WO 96/23811 | 8/1996 |
| WO | WO 00/57721 | 10/2000 |

OTHER PUBLICATIONS

Pileni et al. Chemical Physical Letters 118(4), p. 414-420, 1985.*
International Search Report for PCT/IB2005/003605, mailed Feb. 28, 2006.
Written Opinion for PCT/IB2005/003605, mailed Feb. 28, 2006.

* cited by examiner

*Primary Examiner* — Nissa Westerberg
(74) *Attorney, Agent, or Firm* — Saliwanchik, Lloyd & Eisenschenk (57) ABSTRACT

The present invention relates to a method for the preparation of reverse micelles based on sterols, acylglycerols and metal salt and to reverse micelles obtained thereby. They are advantageously useful in the pharmaceutical and dietetic fields.

18 Claims, 8 Drawing Sheets

REVERSE MICELLE COMPOSITIONS FOR DELIVERY OF METAL CATIONS COMPRISING A DIGLYCERIDE AND A PHYTOSTEROL AND METHOD OF PREPARATION

CROSS-REFERENCE TO RELATED APPLICATIONS

This application claims priority to International Application No. PCT/IB2005/003605, filed on Nov. 2, 2005, which in turn claims priority to Application No. EP 04025987.1, filed on Nov. 2, 2004, the disclosures of which are herein incorporated by reference in their entirety.

FIELD OF INVENTION

The present invention relates to a method for the preparation of reverse micelles based on sterols, acylglycerols and metal salt by mechanical stirring or sonication. Reverse micelles, obtained by the method of the invention, are able to cross mucosa and then cellular membranes. They thus allow internalisation of metal ions by target cells. They are advantageously useful on the industrial level in the pharmaceutical and dietetic fields.

BACKGROUND OF THE INVENTION

Over the last years, various approaches have been proposed to improve the delivery of drugs at the target site. First, the drug must be administered by a suitable and easy route, such as orally or rectally, and second the active ingredient must be delivered at the target cells under an active form. There is no device currently available allowing such a vectorized transport of active molecules.

Many publications and patents describe methods for encapsulating active ingredients into nano- or micro-particles, but the issue, to date unsolved, is on one hand to provide an easy route of administration different from the injectable route, i.e. oral or buccal, and on the other hand to have a quasi complete delivery of the active product at the target sites. The best example of this impossibility is the search made for decades to develop an orally administrated insulin. For instance, the delivery systems disclosed so far have permitted an insulin absorption of 2-5% only.

The inventors have previously uncovered that stirring two types of lipids with some metallic salts allowed to increase salt bioavailability and consequently to obtain same therapeutic activity with 1000 to 5000 times lower doses; the potential toxicity of said salts could then be reduced [see U.S. Pat. No. 6,129,924, WO 02/36134 and WO 2004/075990, for instance].

The inventors in particular discovered that certain products, vegetable fractions or complex of these fractions with metals otherwise inactive or insufficiently active as hypocholesterolaemic agents had a considerably increased activities when they were administered in an olive oil solution. This resulted in seeking among the many components of olive oil those which could lead by mixture or reaction with the tested products to more active products. It is in this way that the inventors were able to identify novel products indicated under the term "organometallic complexes", and obtained by reaction between a derivative of vanadium in oxidation state 4 or 5 and two organic compounds isolated from plant extracts and respectively constituted of sitosterols and acylglycerols.

The inventors also discovered that similar complexes could be prepared from other derivatives of metals wherein the metal is in an oxidation state at least equal to 2 and known for its antidiabetic activity.

They also discovered that similar complexes could be obtained from two types of organic derivatives mentioned previously and various cations of metals useful as biocatalysts in living metabolism, these complexes being, in all the cases, particularly effective agents as vectors of said cations.

"Cations with biocatalytic activity" is understood to cations having a direct biocatalytic activity, and cations capable of substituting for biocatalysts and so modifying certain pathological metabolic pathways. The example of vanadium may be mentioned, which by reason of its similar co-ordination chemistry may substitute for phosphate: thus both acid and alkaline phosphatases are inhibited by vanadyl and vanadate compounds; so too is tyrosine phosphatase which induces a stimulation of the phosphorylation of the tyrosine of the peripheral receptor of insulin as well as of the associated protein kinases.

The present invention now provides a method for preparing reverse micelles, comprising one or more metal salts, such reverse micelles can be administered by any routes, in particular via mucosa and able to cross the cellular membranes. This process advantageously renders possible the control and optimisation of the composition comprising micelles for their later uses in the pharmaceutical and dietetic fields.

SUMMARY OF THE INVENTION

The invention relates to a method for preparing reverse micelles based on sterols, acylglycerols and metal salt, intended to be used in the pharmaceutical and dietetic fields.

The invention also relates to reverse micelles with an aqueous core of less or equal to 100 nm, wherein the said micelles are obtainable by a preparation method comprising:
  (a) Contacting (i) sterol, (ii) acylglycerol, preferably diacylglycerol of fatty acids, (iii) water (in particular purified water), (iv) a metal cation,
  (b) Stirring mixture obtained in step (a), at 40° C. or less, and for a time sufficient to obtain formation of reverse micelles, said stirring being carried out mechanically at a speed from about 1000 to about 5000 r/min or by sonication.

DETAILED DESCRIPTION OF THE INVENTION

Reverse Micelles

The reverse micellar system according to the invention is characterized as a microemulsion comprising a dispersion of water-microdroplets in oil. This dispersion is stabilised by a surfactant (acylglycerol, more preferably diglycerol of fatty acids) at the water/oil interface. The reverse micellar phase can be defined as a system wherein water forms the internal phase and the hydrophobic tails of the lipids form the continuous phase. Reverse micelles containing oil(s), surfactant(s) and an aqueous phase are also characterized as water-in-oil microemulsions.

The size of micelles is controlled by the quantity of solubilized water in the system. It varies in a linear way with the (water)/(surfactant) weight ratio W (solubilized water in the mixture/the surfactant in the mixture). As mentioned above, the ratio W=(water)/(acylglycerol) is preferably less or equal to about 2.5, more preferably less or equal to 1 and more specifically from 0.01 to 0.2. According to a particular embodiment, the ratio W is preferably in the range from 0.05 to 0.18.

The reverse micelles, such as size of the core thereof, can be characterized by various methods:
  X-Ray Scattering
  Neutrons Scattering
  Transmission Electron Microscopy (TEM)
  Dynamic Light Scattering (DLS)

The compounds necessary for the preparation of the reverse micelles according to the invention comprise two lipids: a sterol and an acylglycerol, preferably a diglyceride of fatty acids, which acts as a surfactant. Reverse micelles according to the invention further comprises at least one metal cation.

The ratios of the lipidic constituents (sterols and acylglycerol) can vary in a large extent, for instance the weight ratio sterol/acylglycerol can range from 0.01 to 1 (inclusive). According to a particular embodiment, an excess of acylglycerol (preferably diglyceride of fatty acids) can be used as compared to sterol (preferably sitosterol). More particularly, the weight ratio sterol/acylglycerol is more than or equal to 0.1, more preferably from 0.1 to 0.2.

Metal can be used at very low quantity compared to the two other components, advantageously in a molar ratio of 1/100 to 1/10000 compared to acylglycerol.

The various components can formally be identified by adapted analytical means. Sitosterol can be identified by gas chromatographic analysis, and acylglycerol by high-pressure liquid chromatography (HPLC) using a light scattering detector, on a silica column (kromasil C18), in the presence of an eluent, e.g. isocratic acetonitrile. Gas chromatography can also be used to identify diglycerides.

Reverse micelles are dynamic systems. Brownian motion causes perpetual collisions of micelles, which lead to coalescence of micelles and to exchange of the aqueous cores. Separation and regeneration of micelles occur and allow chemical reactions between different solutions. The exchange rate between micelles increases in particular with temperature, the length of hydrocarbon chains of the surfactant, and W ratio (free water increases said exchange). Within the context of the invention, size of the aqueous core of micelles ranges preferably from 5 to 100 nm. The relative quantity of water in the mixture (W) is preferably lower or equal to 2.5 and preferably lower or equal to 1 of the quantity of acylglycerol, preferably of diglyceride of fatty acids. According to a specific embodiment, the ratio W is preferably from 0.01 to 0.2.

The advantage of reverse micelles of the present invention over delivery systems of the prior art is that the former allows to include therein any type of metal ions.

Method for Preparing Reverse Micelles According to the Invention

In a particular embodiment, the invention relates to a method for preparing reverse micelles presenting an aqueous core of less or equal to 100 nm and comprising a water-soluble pharmaceutical active metal cation, wherein said method comprises the following steps:
  (a) contacting (i) a sterol, (ii) an acylglycerol, preferably a diacylglycerol of fatty acids, (iii) water (in particular purified water), and (iv) a water-soluble metal cation, wherein the ratio W=[purified water]/[acylglycerol, preferably diglyceride of fatty acids] is preferably less or equal to about 2.5,
  (b) stirring mixture obtained in step (a), at 40° C. or less, and for a time sufficient to obtain formation of reverse micelles, said stirring being carried out mechanically at a speed from about 1000 to about 5000 r/min or by sonication.

The obtained and recovered reverse micelles are then particularly useful as a drug delivery system. Step (b) of the process is of particular importance since it allows to obtain reverse micelles, which are then useful as a transport system for delivering drug at the target site in man or animal.

The compounds constituting the reverse micelles are contacted during step (a). Compounds useful in the present invention will be described in more details below.

Stirring of the mixture obtained by step (a) is more particularly carried out at a temperature less than or equal to 40° C., preferably ranging from 30° C. to 38° C., more preferably from 30° C. to 35° C., for a time sufficient to obtain formation of reverse micelles. The time sufficient can vary in particular upon the used stirring techniques, i.e., mechanical stirring at a speed from about 1000 to about 5000 r/min or sonication. The time of mechanical stirring or sonication is anyhow the time needed to convert the initial mixture into a monophasic reversed micellar solution. Stirring by sonication is preferred.

In a particular embodiment, the metal cation is first solubilized in purified water, which is then put into contact with the other constituents (step(a)).

One skilled in the art knows how to select excipients and/or components to be used along with the compositions according to the present invention in order to respect their beneficial properties. In particular, the presence of glycerol can, when introduced in large amount, prevent the formation of reverse micelles or break the micellar system. More specifically, no more than 1%, and preferably no, glycerol (percent expressed by weight of glycerol/total amount by weight of water in the composition) is used for the preparation of the reverse micelles according to the present invention.

Sonication

Ultrasounds of sonication lead to an acoustic cavitation within liquids, i.e., bubbles formation in the liquid. High amplitude of oscillation generates a more important cavitation. Ultrasound produces an homogeneous stirring within all parts of the reaction chamber and provides few turbulence within the liquid. It is the most reliable method to prepare nanoparticles.

Stability of the obtained nanoemulsion is due in particular to acylglycerol (preferably diglyceride of fatty acids) acting as a surfactant.

Different types of sonication materials can be used at the laboratory or industrial scales. High-intensity ultrasound process is the most suitable process. To prepare small quantities, materials of 400 W or 600 W with ultrasounds at 20 kHz give satisfactory results with a good homogeneity of the finished product and are thus preferred. Electronic control of temperature and emission duration of the process is also possible with that type of devices. Materials of the same type exist for industrial uses.

Physical parameters, in particular time (3-5 minutes, in one or more times), are dependent on the used material, volumes of the mixture and viscosity thereof. One skilled in the art can readily define such parameters. More specifically, temperature of the mixture must not exceed 40° C. as to avoid degradation of the reactants. Temperature is preferably lower than about 38° C., even more preferably equal to or lower than about 35° C.

Mechanical Stirring

The usual materials use propellers whose fast movements generate turbulences and swirls allowing the interpenetration of particles, and the formation of nanoparticles within the mixture.

The stirring speed necessary to obtain an optimal result depends on the viscosity of the mixture: stirring speed is preferably ranging from 1 000 to 5 000 r/minute. The implemented volumes, device, stirring speed and W ratio depend on and must be adapted with the pharmaceutically active metal cation introduced.

To optimize this preparation, the mixture is maintained at a temperature lower than approximately 40° C. as to avoid degradation of the reactants, preferably at a temperature lower than approximately 35° C., even more preferably ranging between approximately 30 and 35° C.

Another object of the invention relates to reverse micelles obtainable by the process according to the invention as described above.

Reverse Micelles Compounds

Acylglycerol

Acylglycerols, more particularly acylglycerols of fatty acids, useful for the preparation of the reverse-micellar system according to the invention, can be isolated from the majority of plants and are majority components of plant and animal greasy substances.

The fatty acids number, their position on glycerol, their length of chain and the number of their possible unsaturations vary from one acylglycerol to another. Acylglycerols include in particular mono-, di- or triacylglycerols. In a particular embodiment, mono-, di- or triglycerides used in the present invention present the following formula (I):

in which:
R$_1$ is an acyl residue of a linear or branched, saturated or unsaturated fatty acid having between 14 and 24 carbon atoms, an hydrogen atom, or a mono-, di- or tri-galactose or glucose;
R$_2$ is an acyl residue of a linear or branched, saturated or unsaturated fatty acid having between 2 and 18 carbon atoms,
R$_3$ is an acyl residue of a linear or branched, saturated or unsaturated fatty acid having between 14 and 24 carbon atoms, or an hydrogen atom.

According to a preferred embodiment, at least one of R$_1$ and R$_3$, preferably only one, represents an acyl residue of oleic acid (C18:1[cis]-9).

According to a particular aspect, R$_2$ has one unsaturated bond (e.g; ethylenic bond) and has advantageously 18 carbon atoms, preferably R$_2$ is an oleic acid residue (oleoyl group), one of its positional isomers with respect to the double bond (cis-6,7,9,11 and 13) or one of its iso-branched isomers.

According to another particular aspect, R$_2$ represents an acetyl group.

According to a preferred embodiment, R$_3$ represents an hydrogen atom.

Acylglycerols used in the preparation of micelles according to the invention may be isolated from most plants.

Unsaturated vegetable oils are particularly advantageously used as source of acylglycerols, especially olive oil from the first cold pressing.

As a general rule, an oil containing a high concentration of oleic acid will be chosen as a useful source of acylglycerols according to the invention. Such an oil usually contains a high proportion of acylglycerols useful according to the invention.

According to a particular aspect of the invention, the preferred diglycerides of fatty acids are selected in the group consisting of 1,2-diolein and 1-oleoyl-2-acetyl glycerol.

Acylglycerols, and more particularly those which are found to be the most active in the applications sought after, also exist commercially. This is the case particularly for 1-oleoyl-2-acetylglycerol and 1,2-dioleoylglycerol, which exist as commercial products with a high purity content. In particular, glyceride monooleate containing about 44% of dioleic glycerides, from which about 14% is 1,2-diolein. Such compound is pharmaceutically accepted (*European Pharmacopeia* (4$^{th}$ Edition), *USP* 25/NF20, and *Japanese Standard of food Additives*). Such product is for instance commercially available by Gattefossé Company under the name PECEOL®.

Sterol

The sterols useful for the preparation of the reverse-micellar system according to the invention can be any sterol, and preferably vegetable sterol. Sitosterol is the preferred sterol useful for the reverse-micellar system according to the invention.

The sitosterol incorporated in the reverse-micellar system of the invention can be [beta]- or [gamma]-sitosterol, preferably [beta]-sitosterol, or can be introduced in the form of a plant extract containing at least one of these two forms of sitosterol. Sitosterol is indeed a component of most plants.

It is in particular possible to use various commercial products. More particularly, commercial sitosterol which is extracted from soya can be used. In such a product, the sitosterol generally represents from 50 to 70% by weight of the product and is generally found in a mixture with campesterol and sitostanol in respective proportions in the order of 15% each. Commercial sitosterol which is extracted from a variety of pine called tall oil can also be used, said tall-oil comprising an average of 75% by weight of beta-sitosterol. In general, it will be possible to use the sitosterol in a mixture with sitostanol. Preferably, said mixture comprises at least 50% sitosterol by weight of the mixture.

One will be able to obtain beta-sitosterol having a purity higher than 95%, or even 99%, while proceeding in the following way: one carries out several successive recrystallizations with acetone of commercial mixture, which allows a pre-purification of beta-sitosterol by elimination of the campestanol and of the sitostanol present in the mixture. Then, one subjects the product thus prepurified to 1 to 3 steps of purification by high pressure liquid chromatography on a preparative column C18 by using eluant mixtures, such as methanol, in particular methanol 100% or mixtures of methanol and acetonitrile, in particular of mixtures 80-20 or any intermediate mixture making it possible to obtain sitosterol with a purity higher than 95 or even 99%. This purity is determined by gas chromatography.

Sitosterol and thus sitostanol can also be prepared by extraction from plants according to the techniques in the literature, for example p. 95 of the thesis presented at Montpellier in November 1993 by Claude Cerdon entitled <<*Modulation de la production de sapogénines stéroidiques en réponse a l'inhibition de la synthése de sterols*>>.

This extraction is carried out advantageously by complexation with metals, according to the method described in particular in French patent FR 2 316 247 in which is described a method for isolating 3-hydroxy-steroids and 3-oxo-steroids from a mixture containing these compounds.

To effect this extraction any plant or product of plant origin known for its relatively high content of sitosterol can be used.

By way of examples of plants or products of plant origin with a relatively high free sitosterol content may be mentioned in particular olive oil, soya bean oil cotton leaves, coffee leaves, wheatgerm, for which the free sterol content and the percentage of sitosterol in the free sterol fraction are given in the table below:

| SPECIES | content/kg | % of sterol fraction |
|---|---|---|
| olive oil | 1310 mg | 91% |
| soya oil | 1908 mg | 53% |
| cotton leaves | 3961 mg | 93% |
| coffee leaves | 9914 mg | 51% |
| wheatgerm | 17336 mg | 67% |

% is expressed by weight.

As mentioned above, the ratios of sterol and acylglycerol can vary in a large extent, for instance the weight ratio sterol/acylglycerol can range from 0.01 to 1 (inclusive). According to a particular embodiment, an excess of acylglycerol (preferably diglyceride of fatty acids) can be used as compared to sterol (preferably sitosterol). More particularly the weight ratio sterol/acylglycerol is more than or equal to 0.1, more preferably from 0.1 to 0.2.

Metal

Metal cations which may be used for preparing reverse-micellar system according to the invention are any cation in an oxidation state of at least 2, and whose biocatalytic activity is known or remains to be discovered.

In the context of the present invention, the term "biocatalyst" will indicate these metals exerting a catalytic activity on the biological systems.

Metal ions play an essential part in approximately a third of the enzymes (*Metal Ions in Biological Systems*, Jenny P. Glusker, Amy K. Katz and Charles W. Bock, *The Rigaku Journal*, vol 16, No 2, 1999). They can have different types of actions:
- modification of flows of electrons from the substrate or the enzyme, allowing the control of an enzymatic catalytic reaction,
- connection with the proteinic components of the enzyme to give it a space configuration allowing it to present its active sites,
- to allow an activity of oxidation-reduction when metal has several valences.

Metal M will be selected according to the desired biological activity.

As examples, if a product is sought with hypolipidaemic activity, or hypoglycaemic and/or anti-diabetic and/or insulinomimetic activity, a metallic derivative of vanadium, niobium, molybdenum, selenium, chromium, zinc or titanium will more particularly be chosen.

In these metal derivatives:
- niobium is advantageously in an oxidation state equal to 4 or 5, preferably 5,
- vanadium is advantageously in an oxidation state equal to 3, 4 or 5, preferably 4,
- selenium is advantageously in an oxidation state equal to 4 or 6, preferably 4,
- molybdenum is in general in an oxidation state comprised between 3 and 6, preferably 3,
- chromium is preferably in an oxidation state equal to 3,
- zinc is preferably in an oxidation state equal to 2, 3 or 4.

Examples of metals adapted to other types of activity are indicated below:
- antimony or tin, if the treatment of autoimmune diseases concerning, in particular, the nervous system, for example multiple sclerosis and cancerology, is desired,
- gold, in autoimmune diseases affecting the locomotor system, for example in rheumatoid arthritis,
- vanadium in tumors or neoplasias of the digestive tract, particularly of the pancreas, the colon and the rectum,
- ruthenium or palladium in respiratory tumors or neoplasias,
- lithium in pathologies of the central nervous system, such as Huntington's disease,
- tin, in acquired immunodeficiency syndromes,
- Selenium in cancerology.
- Strontium in osteoporosis.

In a particular embodiment, the metal cation is selected in the group consisting of zinc, niobium, vanadium, selenium, molybdenum, chromium, antimony, tin, gold, ruthenium, palladium, platinum, lithium and strontium.

By way of examples, particularly useful metal derivatives according to the invention are selected from sulphates, hydrates, halides, in particular chlorides, and any other water-soluble salt.

It will be possible in some cases to use ammonium salts, methoxides of alkali metals or alkaline earth metals which can be advantageously dissolved in water or sometimes in alcohols. Organic metal derivatives like acetylacetonates, alkoxides or metal complexes with organic solvents, for example ethers, THF, DMF may also be used. These organic metal derivatives are generally soluble in organic solvents, more particularly in chlorinated solvents like chloroform or dichloromethane. Experiment shows that they can be collected by micelles in a reduced metal form in the aqueous core. However water-soluble salts will be preferred.

Any metal having a water-soluble salt can be introduced into the reverse micelles according to the invention. The choice of metal will vary upon the desired therapeutic activity.

Such an application is as much important that, generally, a man skilled in the art is aware of the inherent difficulties of the therapeutic use of metal cations due to the toxicity of said metal cations in an effective active amount: well-known examples are the lithium salts used in psychiatric or neurologic disorder or the platinum, ruthenium or palladium salts used in cancerology.

As indicated above, a preferred metal is a metal exhibiting a biocatalytic activity. Metal can be used in very low amounts compared to the two other components, preferably in a molar ratio of 1/100 to 1/10 000 compared to acylglycerol.

A therapeutic activity is obtained with amounts of metal divided by 1000 to 10000 compared to the activity obtained with a salt or an organic derivative of the same metal.

Characterisation of Reverse Micelles

The reverse micelles can be physically characterized by various methods:
- X-Ray Scattering
- Neutrons Scattering
- Transmission Electron Microscopy (TEM)
- Dynamic Light Scattering (DLS)

Analysis by X-ray scattering of the products as described in examples 1 and 2 revealed reverse micelles in a micro emulsion.

Use of the Reverse-Micellar System

The reverse micelles of the invention improve bioavailability of the metal cation included therein, allowing its therapeutic or dietetic use with a reduced toxicity or a toxicity equal to zero. This is a considerable advantage compared to the state of the art. Due to its microemulsion nature, the reverse-micellar system allows to provide different types of formulations, comprising various excipients, vehicles or supports, which can be administered by various routes, including per mucosa, for example in a mouth or rectal administration, reverse micelles being then able to cross cellular membranes.

As used herein, the terms "mucosa" and "mucosal" refer to a mucous tissue such as epithelium, lamina propria, and a layer of smooth muscle in the digestive tract. "Mucosal delivery", "mucosal administration" and analogous terms as used herein refer to the administration of a composition to the mucosal tissue. "Mucosal delivery", "mucosal administration" and analogous terms include, but are not limited to, the delivery of a composition through bronchi, gingival, lingual, nasal, oral, vaginal, rectal, and intestinal mucosal tissue.

It is known today that a reverse-micellar system can be used for the preparation of nanomaterials acting as microreactors which thereby enhance reactions of coprecipitations or chemical reductions of ions. They make it possible to prepare nanomaterials in a metastable state, which are usually not formed, in a massive state, at room temperature. It is thus possible to prepare, according to the process of the invention, reduced metal particles of copper, gold, silver, nickel, cadmium, etc., as well as semiconductors, alloys and magnetic fluids.

The dynamic properties of the system make it possible to carry out reactions of reductions of ions in internal volumes of micelles whose size, form and reactivity are finely controlled thanks to the process according to the invention, as indicated above.

The research teams in nanotechnology demonstrated that the aqueous core of a reverse-micellar system behaves as a nanoreactor, i.e. able, at room temperature, to transform a metal salt into a metal in a reduced ionic form, unstable in theory, but fully stable in the core of the micelles.

The major therapeutic activity obtained with very low metal amounts (1 to 10 μg/kg/day in the animal, depending on metals) can be explained by the presence, inside the reverse micelles according to the invention, of metal in a free reduced metallic form, and by the specificity of the lipid components of micelle due to its cellular internalisation. This transformation of metal salt (in general a sulphate) into a reduced free metal particle is a fundamental element allowing metal to have a biological activity of intracellular enzymatic modulation.

Moreover, the activity results obtained in the animal for 4 metals, vanadium in the treatment of diabetes, manganese for an activity "SOD like", strontium to stimulate osseous growth and to treat the osteoporosis, and lithium for neuroprotection to treat in particular Huntington's disease, show that any metal presenting a biological activity can be included in micelles according to the invention for the preparation of pharmaceutical compositions.

According to a first embodiment, the pharmaceutical composition contains reverse micelles as defined previously in a pharmaceutically acceptable support.

According to a particular embodiment, the pharmaceutical composition may comprise a mixture of at least two types of micelles as defined previously, wherein each type comprises a metal cation distinct from the other type.

Such a mixture provides, in certain cases, a synergistic effect: this is the case, in particular, when the composition contains a mixture of zinc and vanadium complex. One could observe, in this case, a synergistic effect while using a pharmaceutical composition containing a mixture of these two types of complexes in the treatment of diabetes (cf. WO 96/23811).

A further object of the invention concerns the use of reverse micelles as defined above for preparing a pharmaceutical composition intended for the delivery, more specifically the mucosal delivery, of one or more metal cation as defined above. The pharmaceutical composition is more particularly intended to prevent or treat one or more symptoms associated with a disease or disorder.

Another object of the invention concerns methods for the delivery of one or more metal cations to an animal, said methods comprising administering to said animal a reverse micelle composition as defined above. In a specific embodiment, the present invention provides methods for the mucosal delivery of one or more metal cations to an animal, said methods comprising mucosally administering to said animal a reverse micelle composition as defined above.

The present invention provides methods for the prevention, treatment, or amelioration of one or more symptoms associated with a disease or disorder, said methods comprising in need thereof an effective amount of a reverse micelle composition as defined above and comprising one or more metal cations useful in the prevention, treatment or amelioration of one or more symptoms associated with said disease or disorder. In a specific embodiment, the present invention provides methods for the prevention, treatment or amelioration of one or more symptoms associated with a disease or disorder, said methods comprising mucosally in need thereof an effective amount of a reverse micelle composition as defined above and comprising one or more metal cations useful in the prevention, treatment or amelioration of one or more symptoms associated with said disease or disorder.

As pharmaceutically acceptable excipient, vehicle or carrier, any excipient vehicle or carrier well-known to the person skilled in the art may be used. The following can be cited as examples in a non-limiting way: lactose, corn starch, glucose, sucrose, sweetening agents such as maltitol syrup, gum arabic, gelatine, carrhagenans, stearic acid, magnesium stearate, dextrin, maltodextrins, mannitol, talc, fats from natural origin, particularly oils of vegetable origin rich in unsaturated fatty acids and sterols. In particular, if eventually necessary, other additives well-known to the person skilled in the art such as stabilisers, drying agents, binders or pH buffers may be used. Preferred excipients in accordance with the invention promote adherence of the finished product to the mucosa.

The compositions of the invention can be administered in different ways, preferably via mucosal tissue, in particular via the oral route with a buccal or digestive absorption. It can also be the rectal route.

In a preferred embodiment of the invention, the reverse micelle compositions of the invention are mucosally administered as a capsule, caplet, aerosol, spray, solution, suspension, emulsion, cachet, tablet, soft elastic gelatin capsule, aerosol, powder or granule. The compositions of the invention can be introduced in liquid form into capsules which releases their contents in the mouth. Preferably, the reverse micelle compositions of the invention are administered to a mammal, more preferably a human to prevent or treat a disease or disorder.

According to another particularly important embodiment, invention also relates to dietetic products, in particular dietetic products useful as food complements to control metabolic dysfunctions, by incorporating the reverse micelles previously defined, as well as a method to prepare these products.

Indeed, these products can be formed easily by contacting, in an oil particularly rich in diglycerides of fatty acids, beta- or gamma-sitosterol or a plant extract containing at least one of said two forms of sitosterol, a metal salt and purified water, and then agitating under the conditions of the process according to the invention as defined previously.

As seen previously, oleic acid C18:1 contents of vegetable oils vary considerably according to the nature of the plant and its geographical origin.

For the preparation of the dietetic products according to the invention, it is advantageously possible to use a vegetable oil in which the oleic acids account for at least 60% of the fatty acids.

According to a preferred embodiment, olive oil will be used, preferably oil of first cold pressure.

Sitosterol will advantageously be introduced under the form of a plant extract. One will be able, in particular, to use a commercial plant extract obtained from soya, or preferably extracted from tall-oil.

To obtain a dietetic product, in particular, usable as a food complement with regulating activity of the glucidic metabolism and/or cardiovascular protective effect, one will use advantageously as metal salt, a salt of vanadium, in which vanadium is in an oxydation state equal to 4, in particular a vanadyl sulphate.

EXAMPLES

Example 1

Preparation of Reverse Micelles Containing Vanadium

To 1.1 g of sitosterol solubilized in 2.2 ml of ethanol, 870 µl of purified water containing 85 µg of vanadyl sulphate (26 µg of metal vanadium) and 40 ml of Peceol® (glyceride monooleate commercially available by Gattefossé) are added.

Sonication of the mixture is carried out for 4 minutes, by monitoring the temperature at less than 38° C.

The W ratio is 0.07.

The obtained product is constituted of a homogeneous mixture of stable reverse micelles containing vanadium.

The analysis by X-ray scattering shows a homogeneous micro emulsion with reverse micelles.

Example 2

Preparation of Reverse Micelles Containing Vanadium for the Treatment of Diabetic Rats To 1.1 g of sitosterol solubilized in 2.2 ml of ethanol, 4.14 ml of purified water containing 85 µg of vanadyl sulphate (26 µg of metal vanadium) and 40 ml of Peceol® are added.

Sonication of the mixture is carried out in two times (3 minutes each), by monitoring the temperature at less than 38° C.

The W ratio is 0.27.

The obtained product is constituted of a homogeneous mixture of stable reverse micelles containing vanadium.

The analysis by X-ray scattering shows a homogeneous micro emulsion with reverse micelles.

Example 3

Preparation of Reverse Micelles Containing Manganese for Assessing a SOD-Like Activity in Animals To 1.1 g of sitosterol solubilized in 2.2 ml of ethanol, 4.14 ml of purified water containing 313 µg of manganese sulphate (102 µg of metal manganese) and 40 ml of Peceol® are added.

The mixture is stirred with a magnetic stirrer heating at 35° C. for 15 minutes.

The W ratio is 0.27.

The obtained product is constituted of a homogeneous mixture of stable reverse micelles containing manganese.

Example 4

Preparation of Reverse Micelles Containing Strontium for Assessing Stimulation of the Osseous Growth Activity in Animals (NP 05 A)

To 5 g of sitosterol solubilized in 20 ml of ethanol, 20 ml of purified water containing 2570 mg of strontium sulphate (1229 mg of metal strontium), 48 ml of Peceol® and 160 ml of olive oil are added.

The mixture is stirred with a magnetic stirrer heating at 35° C. for 15 minutes.

The W ratio is 0.85.

It can then be administered into rats at 2 ml/kg by the rectal route (12.15 mg of metal Sr/24 h/kg).

Example 5

Preparation of Reverse Micelles Containing Strontium for Assessing Stimulation of the Osseous Growth Activity in Animals (NP 05 B)

To 5 g of sitosterol solubilized in 20 ml of ethanol, 20 ml of purified water containing 257 mg of strontium sulphate (133 mg of metal strontium), 48 ml of Peceol® and 160 ml of olive oil are added.

The mixture is stirred with a magnetic stirrer heating at 35° C. for 15 minutes.

The W ratio is 0.85.

It can then be administered into rats at 2 ml/kg by the rectal route (1.21 mg of metal Sr/24 h/kg).

Example 6

Preparation of Reverse Micelles Containing Strontium for Assessing Stimulation of the Osseous Growth Activity in Animals (NP 05 C)

To 5 g of sitosterol solubilized in 20 ml of ethanol, 20 ml of purified water containing 26 mg of strontium sulphate (12.3 mg of metal strontium), 48 ml of Peceol® and 160 ml of olive oil are added.

The mixture is stirred with a magnetic stirrer heating at 35° C. for 15 minutes.

The W ratio is 0.85.

It can then be administered into rats at 2 ml/kg by the rectal route (0.12 mg of metal Sr/24 h/kg).

Example 7

Preparation of Reverse Micelles Containing Vanadium (NP 01 A)

To 1.1 g of sitosterol solubilized in 2.2 ml of ethanol, 1.5 ml of purified water containing 71 µg of vanadyl sulphate (22 µg of metal vanadium), 40 ml of olive oil (4% of diglycerides) are added.

Sonication of the mixture is carried out for 4 minutes, by monitoring the temperature at less than 38° C.

The W ratio is 2.33.

Example 8

Preparation of Reverse Micelles Containing Vanadium (NP 01 B)

To 1.1 g of sitosterol solubilized in 2.2 ml of ethanol, 5.92 ml of purified water containing 85 µg of vanadyl sulphate (26 µg of metal vanadium), 40 ml of Peceol® are added.

Sonication of the mixture is carried out for 4 minutes, by monitoring the temperature at less than 38° C.

The W ratio is 0.38.

Example 9

Preparation of Reverse Micelles Containing Vanadium (NP 01 C)

To 1.1 g of sitosterol solubilized in 2.2 ml of ethanol, 414 µl of purified water containing 85 µg of vanadyl sulphate (26 µg of metal vanadium), 40 ml of Peceol® are added.

Sonication of the mixture is carried out for 4 minutes, by monitoring the temperature at less than 38° C.

The W ratio is 0.04.

Example 10

Preparation of Reverse Micelles Containing Lithium for Protecting the Brain in Huntington's Disease (NP 03)

To 3.6 g of sitosterol solubilized in 5.4 ml of ethanol, 4 ml of purified water containing 9.43 mg of lithium sulphate (600 µg of metal lithium), and 110 ml of Peceol®.

The mixture is stirred with a magnetic stirrer heating at 35° C. for 15 minutes.

The W ratio is 0.1.

It can then be administered into rats at 2 ml/kg by the rectal route (10 µg of metal Li/24 h/kg).

Pharmacological Tests

1—Antidiabetic Activity on Fructose Rats

The model of the fructose rats is a non insulin dependent diabetes (NIDD) similar to the observed human type 2 diabetes.

In this study, the NP 01 product contains reverse micelles based on vanadium, prepared according to example 2. Its therapeutic activity is compared with two reference drugs: Metformin and Rosiglitazone.

Protocol

At D −21, after the period of stalling, rats are weighed and a blood sampling is made to determine the basal values of the biochemical parameters.

The rats are distributed randomly in groups of 10 rats. The drink water is then replaced by a solution of fructose 10% in distilled water. This solution is provided ad libitum for 21 days. They receive then again normal water for the following 21 days of the treatment.

At D 0, animals are weighed and a blood sampling is carried out.

The treatment then starts for a 21-day duration, with a daily administration:

Control group: 1 ml/kg of normal water per os
NP 01 group: 2 ml/kg by the rectal route
Metformin group: 50 mg/kg of Metformin per os.
Rosiglitazone group: 5 mg/kg of Rosiglitazone per os
At D3, blood sample.
At D7, blood sample.
At D 21, blood sample and end of the treatment.

Figure 1:
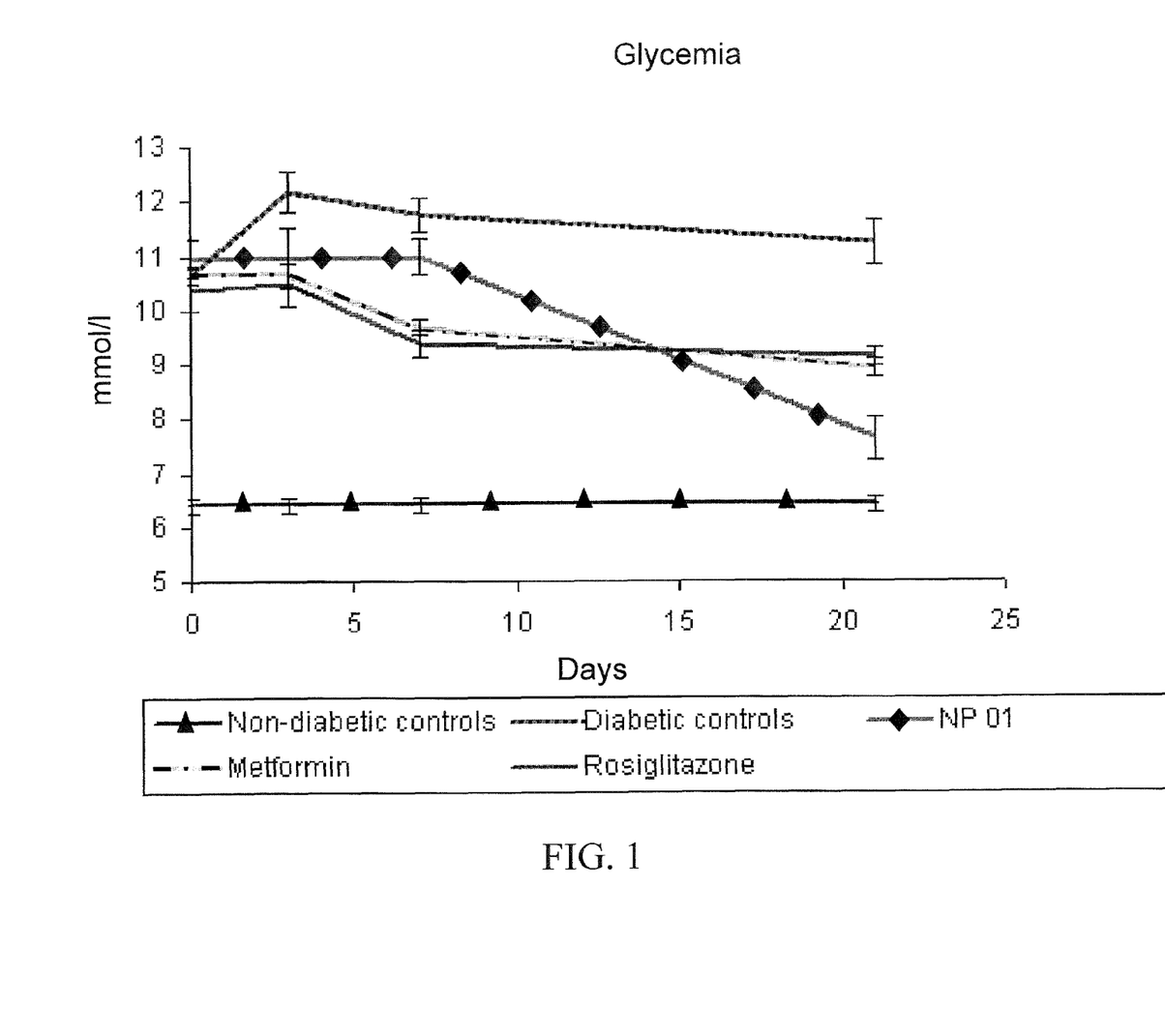
FIG. 1: antidiabetic activity assay on fructose rats of reverse micelles based on vanadium in comparison with reference drugs and controls: glycemia (mmol/l) during treatment (Day)
Figure 2:
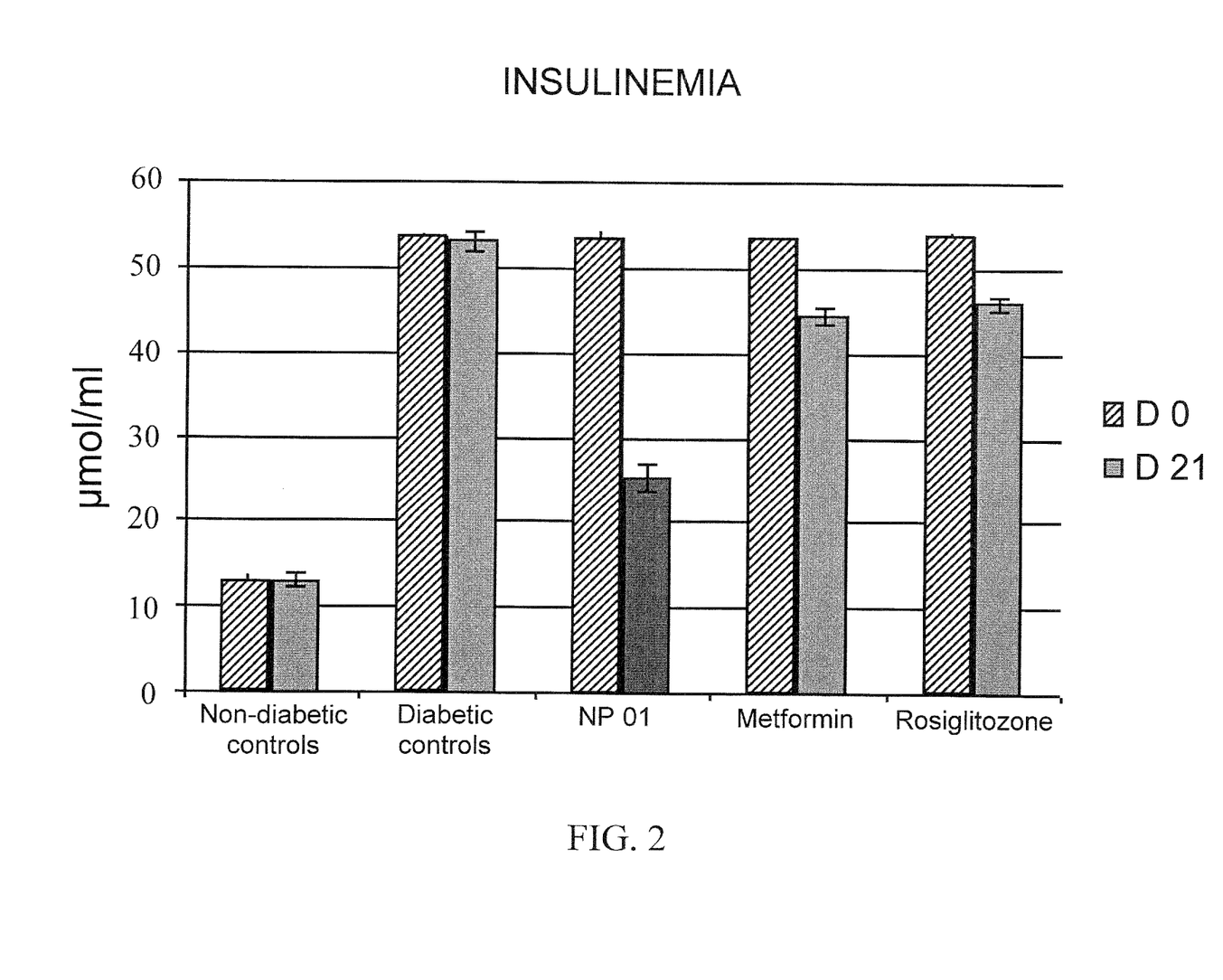
FIG. 2: antidiabetic activity assay on fructose rats of reverse micelles based on vanadium in comparison with reference drugs and controls: insulinemia (µmol/ml) at D0 and D21.

Results (Expressed in mmol/l for Glycemia and µmol/ml for Insulinemia—SD stands for Standard Deviation)—FIGS. 1 and 2 Respectively

| glycemia | D 0 | SD D0 | D3 | SD D3 | D7 | SD D7 | D21 | SD D 21 |
|---|---|---|---|---|---|---|---|---|
| Non-diabetic controls | 6.39 | 0.15 | 6.39 | 0.15 | 6.39 | 0.15 | 6.39 | 0.15 |
| Diabetic controls | 10.65 | 0.15 | 12.18 | 0.36 | 11.76 | 0.31 | 11.22 | 0.4 |
| NP 01 | 10.95 | 0.34 | 10.95 | 0.56 | 10.99 | 0.33 | 7.63 | 0.39 |
| Metformin | 10.64 | 0.17 | 10.63 | 0.22 | 9.68 | 0.15 | 8.91 | 0.16 |
| Rosiglitazone | 10.38 | 0.4 | 10.47 | 0.38 | 9.37 | 0.26 | 9.13 | 0.17 |

| insulinemia | D 0 | SD | D 21 | SD |
|---|---|---|---|---|
| Non diabetic controls | 13.1 | 0.7 | 13.1 | 0.7 |
| Diabetic controls | 53.5 | 0.7 | 53.1 | 1.2 |
| NP 01 | 53.6 | 0.8 | 25.4 | 1.6 |
| Metformin | 53.4 | 0.5 | 44.5 | 1 |
| Rosiglitazone | 53.7 | 0.8 | 46 | 0.8 |

At D 21, all the substances are active. However, the most important effect is observed with NP 01 (example 2 according to the invention), in particular for insulinemia which is the marker of insulino-resistance at the origin of unfavourable evolution of diabetes.

2—<<SOD Like>> Activity on Rats: Test with Adryamycin

The test with adryamycin is a specific test to highlight free anti-radicals activity of a substance. The product contains reverse micelles based on manganese prepared according to example 3.

Protocol

One hour after injection in the leg of a male Wistar rat of 0.2 ml of a solution of adryamycin, a temporary inflammation appears for approximately 12 hours. A second inflammatory phase begins on the 3rd day and lasts for 5 days. The vascular hyperpermeability and the oedema which results therefrom, with a deterioration of the cells of endothelial membranes, are caused by the release of free radicals. The anti-inflammatory steroids and non steroids do not have any action during this second phase. The oedema is measured by plethysmography (expressed by % of pow volume).

Figure 3:
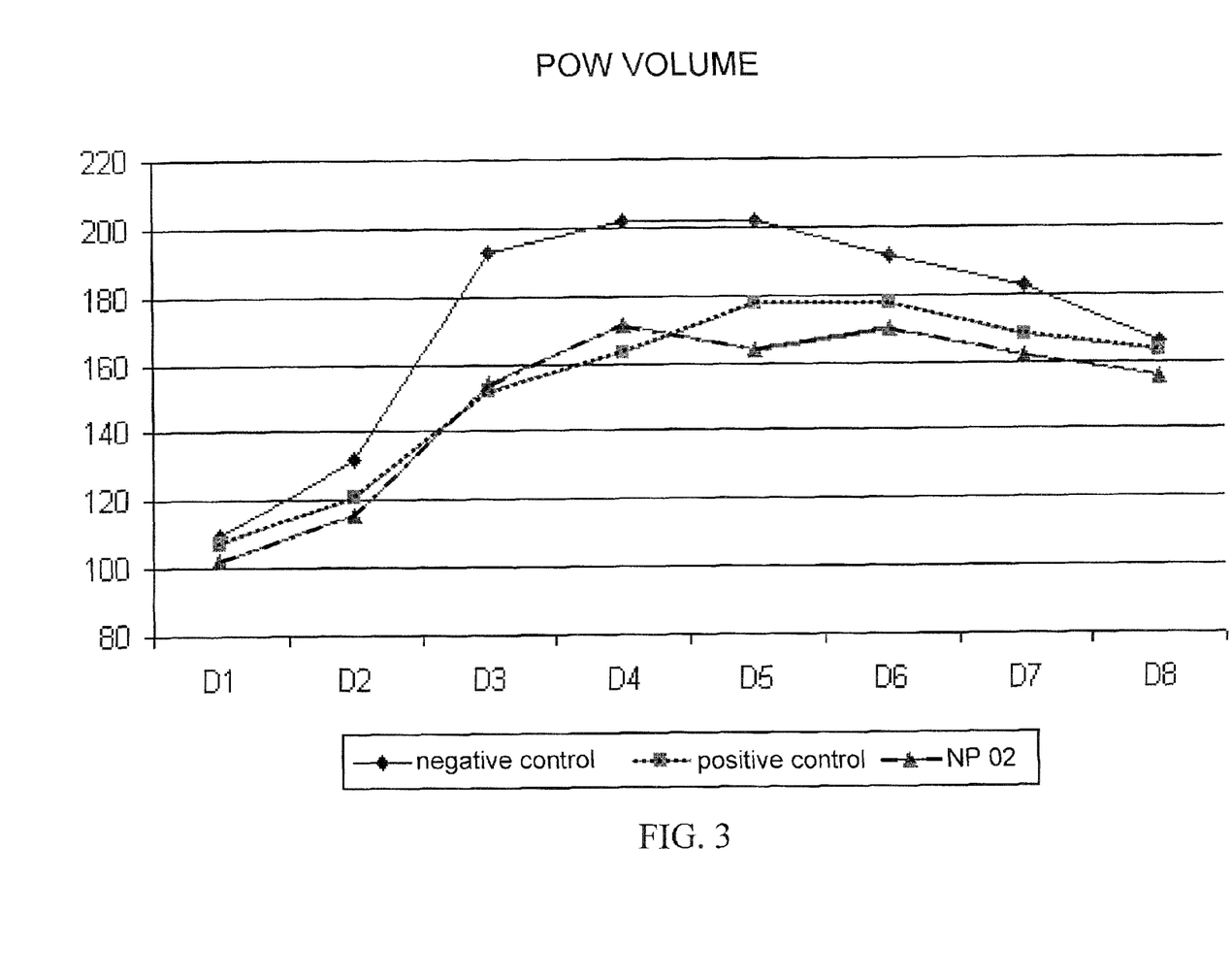
FIG. 3: adryamycin test on Wistar rats with reverse micelles based on manganese in comparison with controls: % of pow volume during treatment

3 batches of 10 rats are made up:
- negative batch controls: olive oil administration (2 ml/kg) by rectal route
- positive batch controls: administration of 100 mg/kg of diosmine
- batch treated by NP 02 (manufactured according to example 3): 2 ml/kg by rectal route Results (SD Stands for Standard Deviation)—FIG. 3

|  | D1 | D2 | D3 | D4 | D5 | D6 | D7 | D8 |
|---|---|---|---|---|---|---|---|---|
| Negative control | 109.3 | 132.3 | 192.8 | 202.1 | 202.1 | 191.6 | 182.3 | 166.2 |
| SD | 9.64 | 10.13 | 16.49 | 17.08 | 24.08 | 16.33 | 12.53 | 12.24 |
| Positive control | 106.7 | 120.8 | 152.2 | 163 | 177.6 | 177.5 | 168.2 | 163.5 |
| SD | 8.25 | 14.96 | 16.61 | 28.71 | 14.58 | 15.38 | 13.46 | 10.58 |
| NP 02 | 102.3 | 115.2 | 154 | 171.2 | 163.6 | 170.3 | 161.5 | 155.5 |
| SD | 8.03 | 14.22 | 13.15 | 17.47 | 29.81 | 20.73 | 20.28 | 14.22 |

The control product Diosmine has a free anti-radical activity similar to Manganese superoxydismutase, (MnSOD); those products are the only products to exhibit an activity on this test. The product NP 02 prepared according to example 3 of the invention has a comparable free anti-radicals activity (even discreetly higher than the reference product).

3—Stimulation of the Osseous Growth on Growing Rats

The objective of this study is the assessment of a stimulation activity of the osseous growth in growing rats.

The product contains reverse micelles based on strontium prepared according to example 4.

Protocol

The animals are Wistar female rats of 200 g (average).

Homogeneous batches of 10 rats are made up starting from their weight.

The treatment is administered once per day during 6 weeks.

Administered batches and products:
- control batch (administration of olive oil by rectal route)
- $SrCl_2$ batch ($SrCl_2$ and strontium ranelate are known active ingredients for the osseous growth and treatment of osteoporosis). 68.2 mg of metal Sr/kg/day are administered by rectal route.
- NP 05 A batch: product prepared according to example 4 of the invention, with 12.5 mg metal Sr/kg/day.
- NP 05 B batch: product prepared according to example 5 of the invention, with 1.21 mg metal Sr/kg/day.
- NP 05 C batch: product prepared according to example 6 of the invention, with 0.12 mg metal Sr/kg/day.

Parameters analyzed at the end of the treatment:
- animals weight
- measurement of the diameter of the rats femoral head after euthanasia and sampling (slide caliper under binocular magnifying glass)
- Strontium amount in bone (by atomic absorption).
- Strontium amount in plasma (by atomic absorption).

Results

Figure 4:
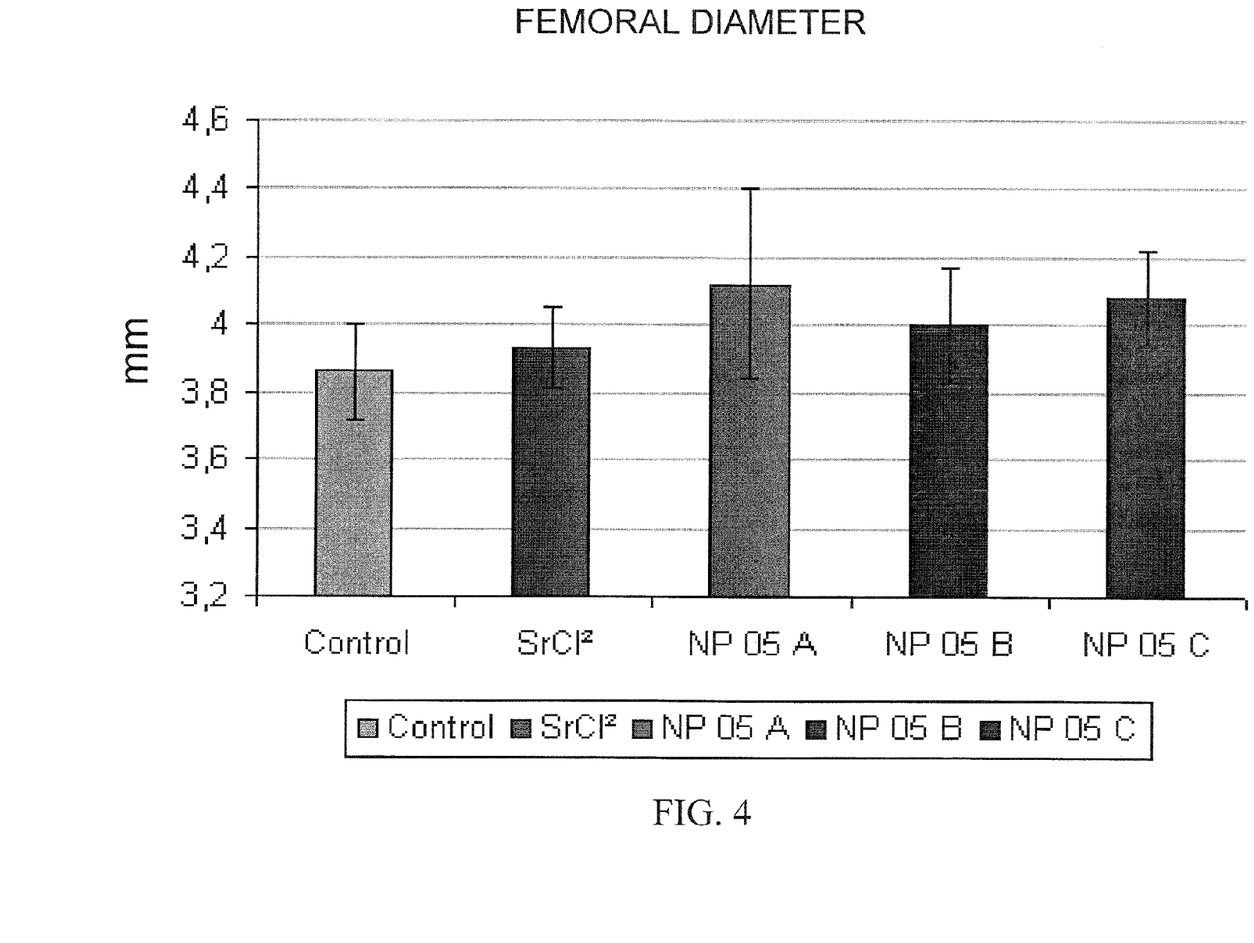
FIG. 4: assessment of a stimulation activity of the osseous growth in growing rats with reverse micelles based on strontium in comparison with control and reference drug: femoral diameter (mm)

Femoral diameter (expressed in mm)—FIG. 4—SD stands for standard deviation

| mm | Control | $SrCl_2$ | NP 05 A | NP 05 B | NP 05 C |
|---|---|---|---|---|---|
| Femoral diameter | 3.86 | 3.93 | 4.12 | 4 | 4.08 |
| SD | 0.14 | 0.12 | 0.28 | 0.17 | 0.14 |

The NP 05 products have a stimulation activity of the osseous growth higher than the reference product. The NP 05 C product has an activity higher than the reference product with 600 times less strontium metal.

Figure 5:
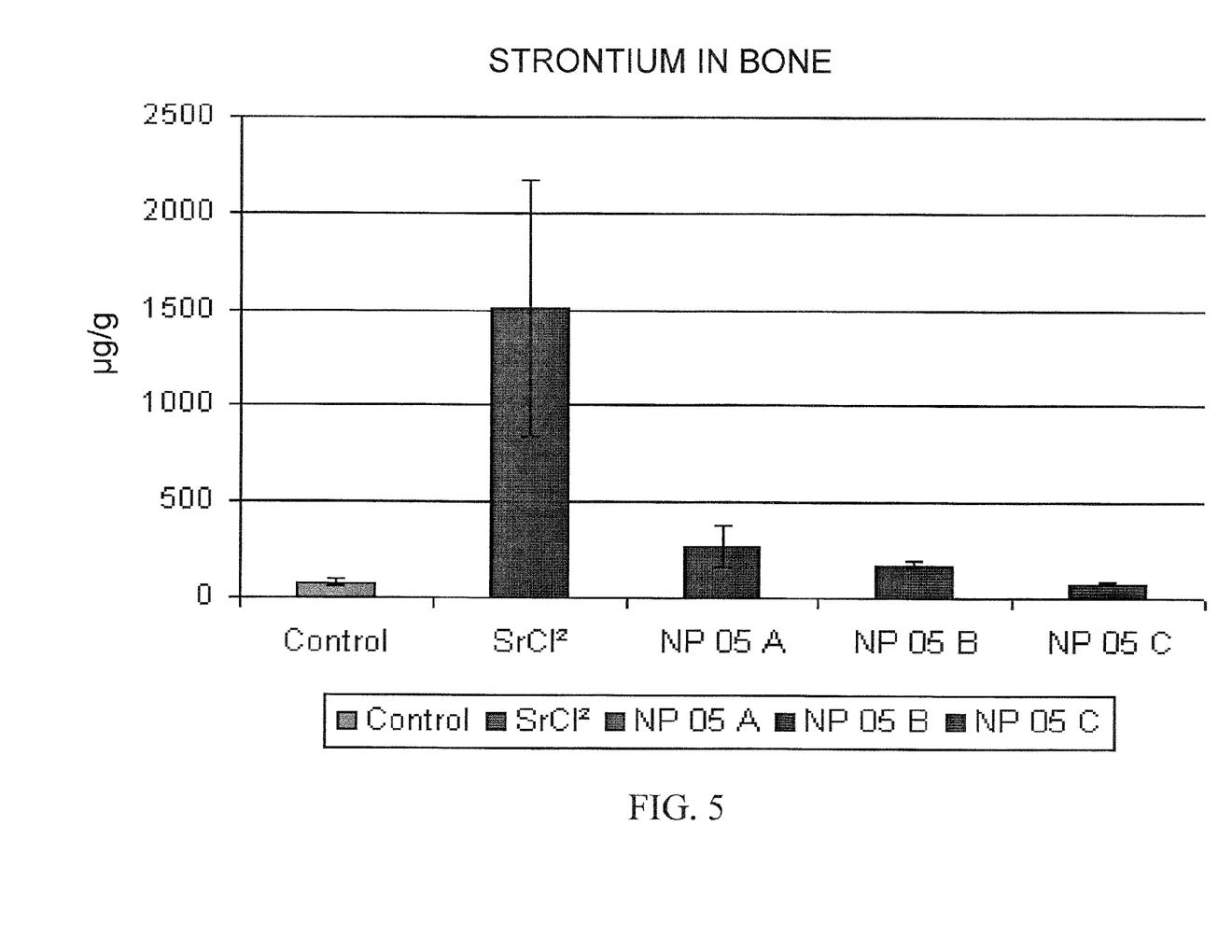
FIG. 5: assessment of a stimulation activity of the osseous growth in growing rats with reverse micelles based on strontium in comparison with control and reference drug: strontium amount in bone (expressed in µg/g)

Strontium amount in bone (expressed in µg/g)—FIG. 5—SD stands for standard deviation

| µg/g | Control | $SrCl_2$ | NP 05 A | NP 05 B | NP 05 C |
|---|---|---|---|---|---|
| Sr in bone | 77.85 | 1508.83 | 261.44 | 172.19 | 77.03 |
| SD | 16.85 | 670.43 | 109.58 | 18.48 | 7.3 |

The negative effect of strontium in the treatment of the osteoporosis (Protelos®) is related to the important fixing of strontium in bone with the therapeutic amounts used (2 g per day for humans and 68.2 mg/kg for animals). The NP 05 product, in particular with the lowest strontium amounts (NP 05 C) does not induce any strontium fixing in bone.

Figure 6:
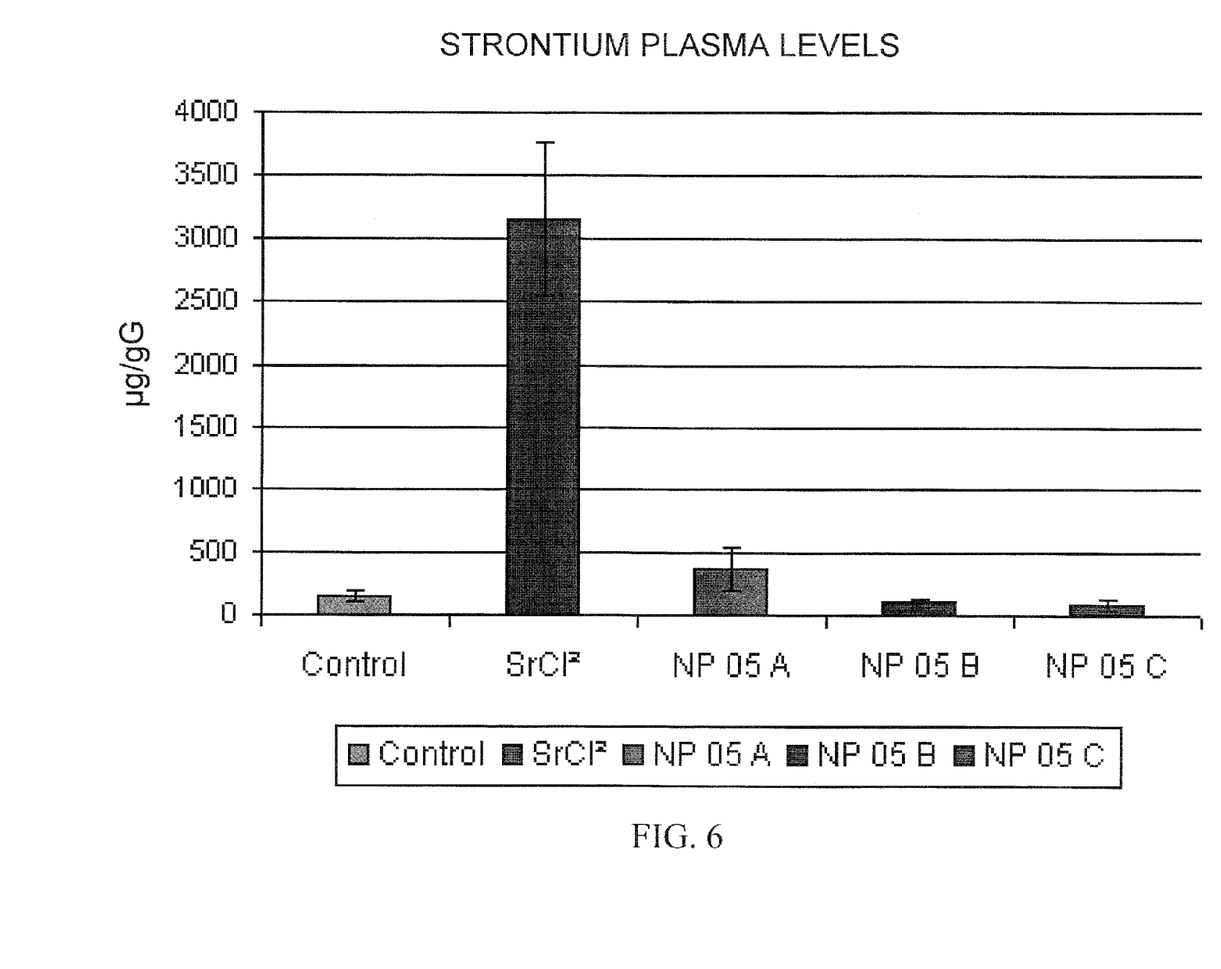
FIG. 6: assessment of a stimulation activity of the osseous growth in growing rats with reverse micelles based on strontium in comparison with control and reference drug: strontium amount in plasma (expressed in µg/g)

Strontium Amount in Plasma (Expressed in µg/g)—FIG. 6—SD Stands for Standard Deviation

| µg/g | µg/g | Control | $SrCl_2$ | NP 05 A | NP 05 B | NP 05 C |
|---|---|---|---|---|---|---|
| Sr plasma levels | Mean | 150 | 3160 | 371 | 101 | 92 |
|  | SD | 41.15 | 599.43 | 165.63 | 37.08 | 43.33 |

The plasmatic strontium rate of the NP 05 C batch prepared according to example 6 of the invention is similar to the rate of the untreated control batch.

4—Neuroprotective Effect of Lithium: Rat Model of Huntington's Disease

Some publications have showed that lithium protects cultured CNS neurons against glutamate mediated by NMDA receptors. In vivo, the neuroprotective effect of lithium against striatal lesion in a rat model of Huntington's disease was assessed. This pharmacological activity is obtained with the same clinical doses that in the treatment of bipolar disorder: 500 mg to 1 000 mg per days of lithium carbonate (lithemia: 0.5-0.8 mEq/l.) in human, and 2-10 mg per day in mice or rats.

Lithium has a high toxicity, and it is necessary to survey the lithemia every day because of the adverse effects.

6 rats receive by rectal route 2 ml/kg per day (product example 10:10 µg Li) 24 h before and during 7 days after the unilaterally infusion of quinolinic acid into the striatum.

Striatum is collected and cryosectionned using a Lecia CM 1850 cryostat. Sectins are treated with ethanol, cleared in xylene and then coverslipped using DPX mountant and allowed to dry.

Sections containing NM neurons are analysed using a stereological program to compare the number of neurons on the lesion side versus the intact side.

At 7 days after QA injection, NP 03 significantly protects NM neurons from death following injection. In previous report, 20/30% cell death was obtained in saline treated subjects. Here, only 9,2% of cell death with NP 03 administration is obtained.

A result similar to the results obtained with lithium chloride administered by IP route is obtained, but only 10 µg/day is used instead of 10 mg/day lithium metal.

Optimization of Pharmacological Activity Depending on Micellar Size

A pharmacological study was carried out on the STZ rats model as to compare activity of 5 products prepared according to the invention, wherein the water amount introduced into the mixture is the only variable parameter (the same quantity of solubilized vanadyl sulphate is used). It follows therefrom that the only difference between these 5 products is the size of the reverse micelles.

The STZ rats model is a mix model for type 1 and type 2 diabetes. This model allows to obtain a quick response on antidiabetic activity of substances.

Protocol

Streptozotocine (STZ) is administered to Wistar males rats from 250 to 300 g, by IV way in an amount of 50 mg/kg. 3 days after the administration of STZ, the animals glycemia lies between 20 and 30 mmol/l, and remains stable during the following 7 days. The studied products are administered daily for 7 days. Glycemia is measured at D0, D1, D3 and D7.

Each batch corresponds to 6 rats.
control batch: olive oil in emulsion with water by rectal route
batch A: administered by rectal route [2 ml/kg (W=2.30)]: example 7
batch B: administered by rectal route [2 ml/kg (W=0.38)]: example 8
batch C: administered by rectal route [2 ml/kg (W=0.04)]: example 9
batch D: administered by rectal route [2 ml/kg (W=0.90)]
batch E: administered by rectal route [2 ml/kg (W=0.125)]

Results

| Glycemia (mmol/l) | W | D0 | D3 | D7 |
| --- | --- | --- | --- | --- |
| Control batch | | 21.02 | 21.93 | 20.03 |
| | | SD 2.66 | SD 3.36 | SD 2.19 |
| Batch A | 2.30 | 27.56 | 24 | 19.8 |
| | | SD 0.96 | SD 1.27 | SD 2.09 |
| Batch D | 0.90 | 21.1 | 14 | 12.20 |
| | | SD = 1.10 | SD = 1.32 | SD = 1.64 |
| Batch B | 0.38 | 21.54 | 16.31 | 13.44 |
| | | SD 0.90 | SD 0.78 | SD 0.81 |
| Batch E | 0.125 | 17.6 | 11.80 | 8 |
| | | SD = 1.18 | SD = 1.22 | SD = 1.45 |
| Batch C | 0.04 | 22.13 | 20.55 | 14.70 |
| | | SD = 1.84 | SD = 1.70 | SD = 2.26 |

Figure 7A:
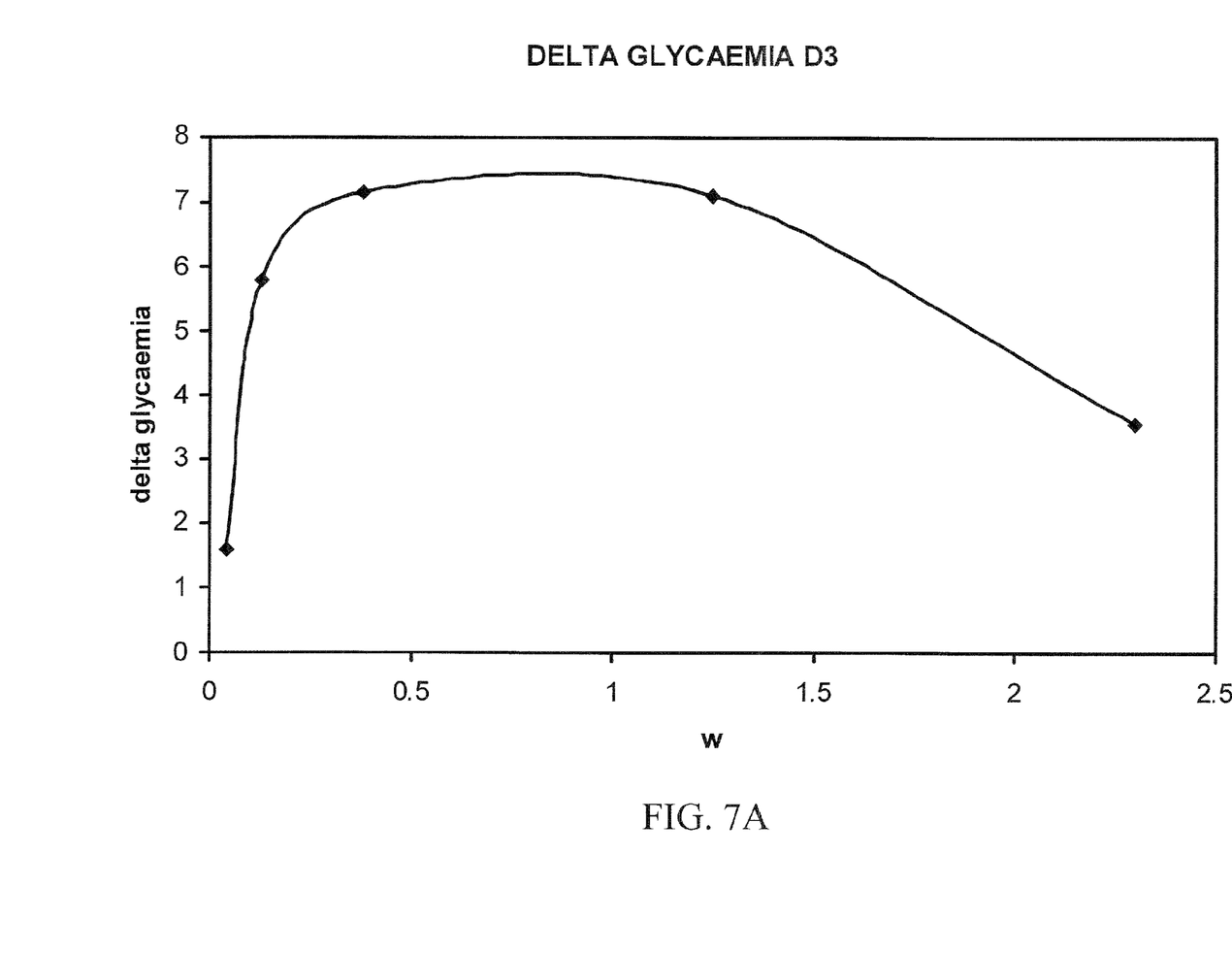
FIGS. 7A and B: glycemia obtained on the STZ rats model at D3 and D7 respectively depending on W ratio of the administered reverse micelles containing vanadium The following examples are intended to exemplify the operation of the present invention but not to limit its scope.
Figure 7B:
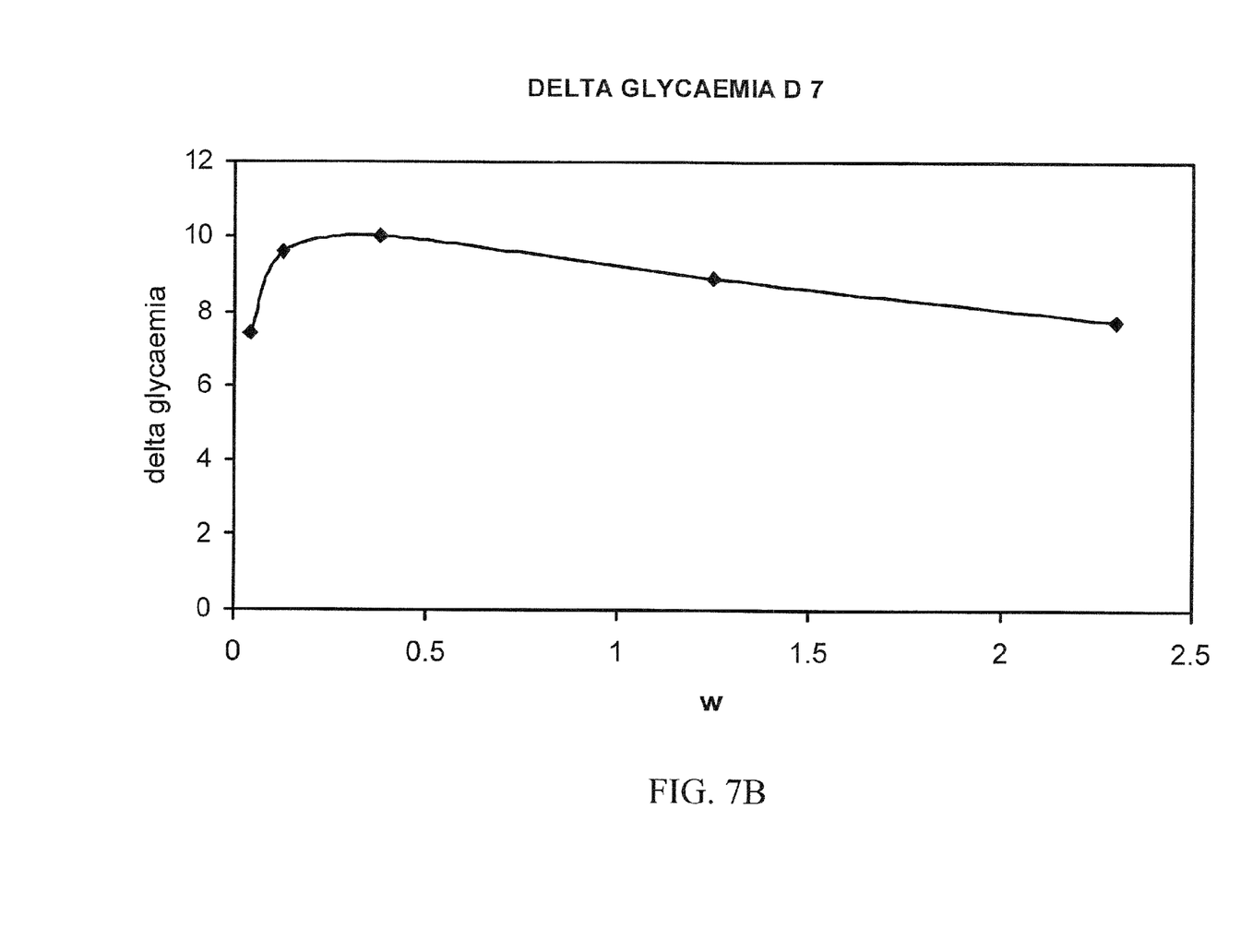

FIGS. 7A and 7B represent the glycemia obtained at D3 and D7 respectively.

Comments

The most important antidiabetic activity appears to be obtained when ratio W ranges from 0.12 and 1.

Higher sized micelles contain free water wherein metal is no longer under a reduced metallic form and remains in a sulphate form which produces a lower activity.

Upon variation of the size of micelles (W ratio), activity of the prepared product according to the invention can be optimized.

Optimization of Incorporated Water Quantity

Protocol

Samples containing the relative quantities of peceol, sitosterol and ethanol given in the above examples were prepared by varying quantity of water in which metal ions were solubilized. A dilution scale was made by increasing quantity of water with increment of 0.3%.

Samples were homogenized by stirring at 35° C., as described above.

The impact of the quantity of water on the stability of the reverse-micellar system was determined visually (turbidity) and by small-angle X-ray diffraction.

Result

From 6.9% water in the composition (i.e., W is about 0.175) and more, the microemulsion is becoming more and more turbid and two phases are appearing where water amount is increasing. The percent of water is expressed by weight of total water: total weight of the composition.

The invention claimed is:

1. A method for preparing reverse micelles with an aqueous core of less than or equal to 100 nm, comprising:
   (a) contacting (i) beta-sitosterol, (ii) an acylglycerol, (iii) water, (iv) ethanol, and (v) a water-soluble metal cation to form a mixture, and
   (b) stirring the mixture obtained in step (a), at 40° C. or less, and for a time sufficient to obtain formation of reverse micelles, said stirring being carried out mechanically at a speed from about 1000 to about 5000 r/min or by sonication,
wherein water and acylglycerol are present in a ratio W=(water)/(acylglycerol) of less than or equal to about 2.5.

2. The method according to claim 1, wherein the acylglycerol is a diacylglycerol of fatty acids.

3. The method according to claim 2, wherein the diacylglycerol of fatty acids is 1-2 diolein or 1-oleoyl-2-acetyl-glycerol.

4. The method according to claim 1, wherein the metal is capable of forming a water-soluble salt.

5. The method according to claim 1, wherein the metal is a metal exhibiting a biocatalytic activity.

6. The method according to claim 1, wherein the W ratio is from 0.05 to 0.18.

7. The method according to claim 1, wherein the stirring of the mixture is carried out at a temperature between approximately 30 and 35° C.

8. The method according to claim 1, wherein the metal cation has an oxidation state of at least 2.

9. The method according to claim 1, wherein the metal cation is zinc, niobium, vanadium, selenium, molybdenum, chromium, antimony, tin, gold, ruthenium, palladium, platinum, lithium or strontium.

10. Reverse micelles obtainable by the method according to claim 1.

11. A pharmaceutical composition comprising reverse micelles as defined in claim 10 in a pharmaceutically acceptable carrier.

12. The method according to claim 1, wherein the water is purified water.

13. The method according to claim 1, wherein the ratio W is less than or equal to 1.

14. The method according to claim 1, wherein the ratio W is from 0.01 to 0.2.

15. The method according to claim 9, wherein the metal is strontium.

16. The reverse micelle according to claim 10, wherein the reverse micelles have a ratio W that is less than or equal to 1, wherein W=(water)/(acylglycerol).

17. The reverse micelle according to claim 16, wherein the ratio W is from 0.01 to 0.2.

18. The composition according to claim 11, wherein said reverse micelles have a ratio W, wherein W=(water)/(acylglycerol), that is:
   a) less than or equal to 1; or
   b) from 0.01 to 0.2.

* * * * *

UNITED STATES PATENT AND TRADEMARK OFFICE
CERTIFICATE OF CORRECTION

| | |
|---|---|
| PATENT NO. | : 9,173,838 B2 |
| APPLICATION NO. | : 11/718511 |
| DATED | : November 3, 2015 |
| INVENTOR(S) | : Jean-Claude Maurel |

Page 1 of 1

It is certified that error appears in the above-identified patent and that said Letters Patent is hereby corrected as shown below:

Specification

<u>Column 5,</u>
Line 49, "(C18:1[cis]-9)." should read --(C18: 1[cis]-9).--.

Signed and Sealed this
Fifth Day of April, 2016

Michelle K. Lee
*Director of the United States Patent and Trademark Office*